(12) United States Patent
Kumar et al.

(10) Patent No.: US 11,774,383 B2
(45) Date of Patent: Oct. 3, 2023

(54) QUICK NMR METHOD FOR IDENTIFICATION AND ESTIMATION OF COMPONENTS IN HAND-RUB FORMULATIONS

(71) Applicant: Indian Oil Corporation Limited, Mumbai (IN)

(72) Inventors: Ravindra Kumar, Faridabad (IN); Sujit Mondal, Faridabad (IN); Christopher Jayaraj, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 60 days.

(21) Appl. No.: 17/364,203

(22) Filed: Jun. 30, 2021

(65) Prior Publication Data
US 2022/0003698 A1  Jan. 6, 2022

(30) Foreign Application Priority Data
Jul. 1, 2020 (IN) .............................. 202021027916

(51) Int. Cl.
*G01N 24/08* (2006.01)
*G01R 33/46* (2006.01)

(52) U.S. Cl.
CPC ......... *G01N 24/087* (2013.01); *G01N 24/084* (2013.01); *G01R 33/4625* (2013.01)

(58) Field of Classification Search
CPC .. G01N 24/087; G01N 24/084; G01N 24/085; G01N 24/082; G01R 33/4625; A61K 8/22; A61K 8/34; A61K 8/345; A61Q 17/005

See application file for complete search history.

(56) References Cited

U.S. PATENT DOCUMENTS 8,380,445 B2  2/2013  Raftery et al.
8,795,697 B2  8/2014  Brown
(Continued)

FOREIGN PATENT DOCUMENTS

CN  107561111 B  11/2019
JP  2013018952 A  1/2013

OTHER PUBLICATIONS

Monakhova et al., Rapid 1H NMR Determination of Hydrogen Peroxide in Cosmetic Products and Chemical Reagents, Anal. Methods, 8, 4632. (Year: 2016).*

(Continued)

*Primary Examiner* — Gregory H Curran
(74) *Attorney, Agent, or Firm* — Workman Nydegger

(57) ABSTRACT

The present invention relates to a method based on proton NMR technique to differentiate genuine and spurious Hand-rub formulations. This method identifies and estimates all four components present in WHO-recommended Hand-rub formulations. Further, this method also identifies the presence of non-recommended/additional components present in WHO-recommended Hand-rub formulations. The method described in this invention utilizes experimental parameters and derived equations to quantify all four components in just fifteen minutes without using any organic solvents.

10 Claims, 1 Drawing Sheet

(56) References Cited

U.S. PATENT DOCUMENTS

| | | | |
|---|---|---|---|
| 9,775,346 B1 | 10/2017 | Mouser | |
| 2005/0062471 A1* | 3/2005 | Early | G01N 24/08 324/307 |

OTHER PUBLICATIONS

"Fostering Discover with a PicoSpin 45 Spectrometer" Thermo Fisher Scientific (www.thermofisher.com/us/en/home/industrial/... .../spectroscopy-elemental-isotope-analysis-resource-library/nmr-tech-talk/nmr-tech-talk-april-2014/fostering-discovey-picospin-45-spectrometer.html) Obtained Jun. 7, 2023 (Year: 2014).*

"NMR picoSpin Spectrometer Frequently Asked Questions Revision B" Thermo Fischer Scientific (Year: 2013).*

India Examination Report, dated Feb. 23, 2022, from India Patent Application No. 202021027916.

Canadian Office Action, dated Sep. 7, 2022, from Canadian Patent Application No. 3123183.

Japanese Office Action, dated Jan. 24, 2023, from Japanese Patent Application No. 2021-102244.

Bonjour et al., "Introducing High School Students to NMR Spectroscopy through Percent Composition Determination Using Low-Field Spectrometers", Journal of Chemical Education, vol. 92, pp. 529-533, https://pubs.acs.org/doi/10.1021/ed500731y, Jan. 30, 2015 (Jan. 30, 2015).

U.S. Department of Health and Human Services, "Temporary Policy for Preparation of Certain Alcohol-Based Hand Sanitizer Products During the Public Health Emergency (COVID-19)", Health Policy and Services Research, pp. 1-15, https://www.hhs.gov/guidance/document/guidance-industry-temporary-policypreparation-certain-alcohol-based-hand-sanitizer, Mar. 2020.

Rackham D: "Quantitative analysis in pharmacy and pharmaceutical chemistry by nuclear magnetic resonance spectroscopy", TALANTA, vol. 17, No. 10, Mar. 16, 1970, pp. 895-906, XP055858244, NL ISSN: 0039-9140, DOI: 10.1016/0039-9140(70)80132-1 * section "Analysis Without a Reference Standard" on pp. 902-904; p. 895-p. 898 *.

U.S. Department of Health and Human Services, Food and Drug Administration: "Contains Nonbinding Recommendations Temporary Policy for Preparation of Certain Alcohol-Based Hand Sanitizer Products During the Public Health Emergency (COVID-19) Guidance for Industry Pharmaceutical Quality/Manufacturing Standards (CGMP)/Over-the-Counter (OTC) Contains Nonbinding Recommendations", Mar. 2020, pp. 1-19, XP055858180, Retrieved from the Internet: URL:https://web.archive.org/web/20200620164135if/https://www.fda.gov/media/136289/download.

World Health Organization and "Who Guidelines on Hand Hygienein HealthCare", Jan. 15, 2009, p. 49, [online], [Reiwa 4Jul. 28, 2022 search], the Internet<URL:https://apps.who.int/iris/bitstream/handle/10665/44102/9789241597906_eng.pdf> (Document showing a well-known technique).

Does it Know Correctly about Goods Which Appealed for Disinfection or Disinfection? It Relates to—New Style Coronavirus—the website of independent administrative institution National Consumer Affairs Center of Japan, May 15, 2020, [online], [Reiwa 4Jul. 28, 2022 search], the Internet<URL:https://www.kokusen.go.jp/news/data/n20200515_2.html>.

[ Ratio / of NMR / Integration ] Website [ of a UBE, Inc. chemical-analysis center ], Oct. 13, 2014, [online], [Reiwa 4Jul. 28, 2022 search], and Internet <https://web.archive.org/web/20141013171103/https://www.ube-ind.co.jp/usal/documents/o469_142.htm>.

Donald L. Pavia et al., "Introduction to Spectroscopy" "", Fourth Edition, 2001.

Robert M. Silverstein, "Spectrometric Identification of Organic Compounds", 1963.

https://docbrown.info/page06/spectra/propan-2-ol-nmr1h.htm, May 10, 2021.

https://www.chegg.com/homework-help/questions-and-answers/following-h-nmr-spectrum-assignment-glycerol-unequal-vicinal-coupling-evidence-hindered-fr-q87451987, Feb. 23, 2022.

* cited by examiner

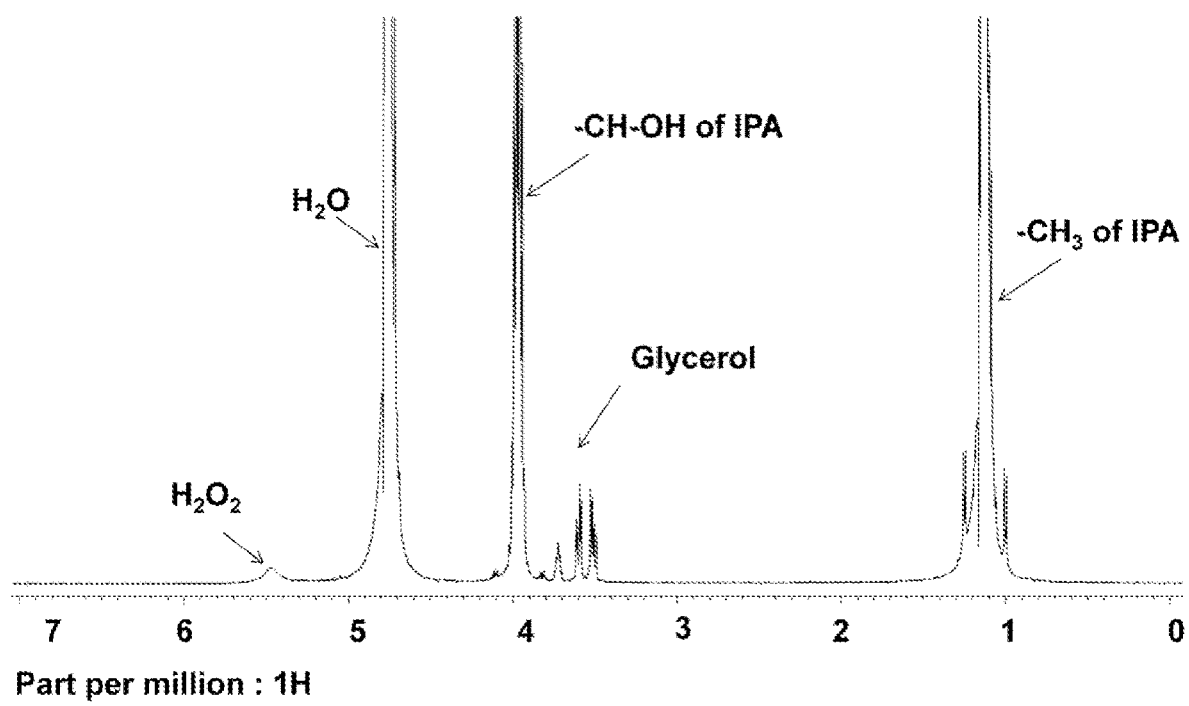

QUICK NMR METHOD FOR IDENTIFICATION AND ESTIMATION OF COMPONENTS IN HAND-RUB FORMULATIONS

FIELD OF THE INVENTION

The invention relates to a method based on proton NMR technique to differentiate genuine and spurious Hand-rub formulations. This method identifies and estimates all four components present in WHO-recommended Hand-rub formulations. Further, this method also identifies the presence of non-recommended/additional components present in Hand-rub formulations.

BACKGROUND OF THE INVENTION

In light of rapidly evolving COVID-19 pandemic and demand for Hand-rub formulations in global and Indian markets, many companies are manufacturing alcohol-based Hand-rub formulations and selling in the market. Though manufacturers produce and supply Hand-rub formulations as per guidelines by WHO, due to sudden demand, poor quality spurious Hand-rub formulations are also available in market which violets WHO guidelines. Considering this aspect, there is a need for quick and reliable method to analyze the alcohol-based Hand-rub formulations by analytical technique for quality control.

WHO recommended two Hand-rub Formulations with Formulation I having final composition (v/v): as Ethanol (80%), Hydrogen peroxide (0.125%), Glycerol (1.45%), Sterile distilled or boiled cold water; and Formulation II having final composition (v/v): Isopropanol (75%), Hydrogen peroxide (0.125%), Glycerol (1.45%), Sterile distilled or cold, boiled water.

After the final formulations are made, it is desirable to estimate the composition of the formulation to confirm that the required composition has been achieved. It is a very important step in quality control. As per the WHO's "Guide to Local Production: WHO-recommended Hand-rub Formulations", an alcoholmeter can be used to control the alcohol concentration of the final use solution. Hence, only the alcohol concentration in the final formulation can be identified.

U.S. Pat. No. 8,795,697 describes a sanitizer composition and its method of preparation. It discloses the composition and its preparation by simply mixing together the correct quantities of alcohol, water and thickener and an activating agent to create a substantially thick liquid or gel of the desired viscosity. However, this document does not disclose any methodology for analyzing the final composition of the sanitizer prepared.

U.S. Pat. No. 8,380,445 describes the method based on two-dimensional NMR for differentiating complex mixtures having one or more chemical species. This method directs toward high-resolution NMR analysis of chemical structures, and more particularly to the use of selective total correlation spectroscopy ("TOCSY") to quantify and analyze a predetermined set of chemical species. 2D NMR is a long experiment and requires stringent conditioning of the NMR spectrometer.

CN 107561111 describes the methodology for detection of cassava syrup when mixed in honey. Extraction of the sample is done following the procedure described in the invention. Proton NMR is performed on the sample having a particular pH value. By analyzing the chemical shift of honey sample marker, it is determined whether honey is adulterated with cassava syrup or not.

U.S. Pat. No. 9,775,346 invention relates to sanitizers, specifically a hand sanitizer composition and method of manufacture. The composition includes a soothing agent in a therapeutically significant amount and a conditioner. But this invention does not disclose any methodology for analyzing the final composition of the sanitizer prepared.

Nuclear magnetic resonance (NMR) spectroscopy is a well-known technique that provides highly detailed information on molecular structure. NMR is also quantitative because the detected signal is linearly proportional to the absolute number of active nuclei in the detected sample volume. Thus, relative numbers of hydrogen, carbon, or other atoms in a molecule can be directly measured, the relative number of different molecular species in a mixture can be computed, and by using an internal standard, the absolute concentration of species can be calculated.

There is a need for an analytical method which is quick, reliable, and obtainable using one technique for quality control of hand sanitizer formulations. In open literature, each component as recommended in the hand sanitizer formulation is identified using different techniques and analytical methods. Hydrogen peroxide concentration is measured by titrimetry (oxidoreduction reaction by iodine in acidic conditions). A higher-level quality control can be performed using gas chromatography and titrimetric method to control the alcohol and the hydrogen peroxide, respectively in hand sanitizers. However, these methods take four to five hours to test one sample and require chemicals such as iodine and acids. Further, the identification of glycerol/glycerin and water becomes quite challenging as they cannot be analyzed by these methods. There is no single method available to measure all four components and impurity of toxic chemicals such as methanol in WHO-recommended disinfectant formulations.

SUMMARY OF THE INVENTION

In an aspect of the present invention, the present invention discloses a method for identifying and quantifying components in a hand-rub formulation, the method comprising, analyzing and characterizing the components by determining position of hydrogen attached to different atoms in each component based on proton NMR technique to obtain chemical shift of hydrogen as ppm peak results, quantifying the components using experimental parameters and solving equations with the results obtained in step a) to arrive at the weight % of each component, wherein weight % refers to the percentage by weight of each component in the hand-rub formulation.

In a feature of the present invention, the components in the hand-rub formulation are an alcohol, a peroxide, glycerol, and water.

In a feature of the present invention, method comprises analyzing and characterizing an alcohol, analyzing and characterizing a peroxide, analyzing and characterizing glycerol, analyzing and characterizing water.

In a feature of the present invention, alcohol is ethanol or isopropanol, and peroxide is hydrogen peroxide.

In a feature of the present invention, the chemical shift of —OCH— signal of secondary hydrogen at 4.0 ppm is used for quantification of isopropanol, chemical shift of —OCH— peak at 3.76 ppm is used for quantification of glycerol, chemical shift of —OH at 5.5 ppm is used for quantification of hydrogen peroxide, and chemical shift of —OH at 4.77 ppm is used quantification of water.

In a feature of the present invention, the chemical shifts in the proton NMR at 3.0 ppm to 6.0 ppm corresponding to isopropanol, glycerol, water, and hydrogen peroxide are used for quantification. In a feature of the present invention, the weight % of each component in a hand-rub formulation based on isopropanol has been quantified by the equation IT=IP+IG+IW+IH, and wherein IT is total integral, IP is Ip×molecular weight of isopropanol, IG is Ig×molecular weight of glycerol, IW is Iw×molecular weight of water, IH is Ih×molecular weight of hydrogen peroxide, wherein Ip, Ig, Iw and Ih are "one proton integral intensity" of isopropanol, glycerol, water, and hydrogen peroxide and is calculated by corresponding integral intensity of proton NMR spectrum divided by number of protons of the group.

In a feature of the present invention, Ip is an integration of 4.0 ppm peak, Ig is an integration of 3.76 ppm peak, Iw is an integration of 4.77 ppm peak divided by two after subtraction of isopropanol and glycerol —OH contributing protons, Ih is an integration of 5.5 ppm peak divided by two.

In a feature of the present invention, weight % of Isopropanol=(IP/IT)×100, weight % of Glycerol=(IG/IT)×100, weight % of Water=(IW/IT)×100, weight % of hydrogen peroxide=(IH/IT)×100.

In a feature of the present invention, weight % of each component in a hand-rub formulation based on ethanol has been quantified by the equation IT=IE+IG+IW+IH, and wherein IE is Ie×molecular weight of ethanol, IG is Ig×molecular weight of glycerol, IW is Iw×molecular weight of water, and IH is Ih×molecular weight of hydrogen peroxide.

In another feature of the present invention, Ie, Ig, Iw and Ih are "one proton integral intensity" of ethanol, glycerol, water, and hydrogen peroxide and is calculated by corresponding integral intensity of proton NMR spectrum divided by number of protons of that group.

In another feature of the present invention, Ie is an integration of 1.14 ppm peak divided by three, Ig is an integration of 3.8 to 3.4 ppm peak–Ie×two, Iw is an integration of 4.7 ppm peak divided by two after subtraction of ethanol and glycerol —OH contributing protons, Ih is an integration of 5.4 ppm peak divided by two.

In another feature of the present invention, weight % of Ethanol=(IE/IT)×100, weight % of Glycerol=(IG/IT)×100, weight % of Water=(IW/IT)×100, weight % of hydrogen peroxide=(IH/IT)×100.

In another feature of the present invention, method based on proton NMR comprises identification and quantification of all components in a hand sanitizer formulation and provides equations for quantification of components in a hand sanitizer formulation.

In another feature of the present invention, the chemical shift of proton NMR spectrum of the hand sanitizer formulation used is in the range of 0.0 ppm to 10.0 ppm.

In another feature of the present invention, method based on proton NMR further comprises identification of methanol in a hand sanitizer formulation, and a sharp singlet is observed at 3.3 ppm of —OCH3 for methanol.

OBJECTIVES OF THE INVENTION

A primary objective of the invention is to provide a quick and reliable method for quality control and to differentiate genuine and spurious hand sanitizers based on proton NMR technique.

A further objective of the invention is to provide a NMR method which estimates all four components (Ethanol or isopropanol, Glycerol, Hydrogen peroxide and water) in WHO-recommended Hand-rub Formulations.

Another objective of this invention is to provide a method that yield results based on proton NMR, makes use of only one sample, is reliable and allows quantification to be done within fifteen minutes.

BRIEF DESCRIPTION OF DRAWINGS

To further clarify advantages and aspects of the invention, a more particular description of the invention will be rendered by reference to specific embodiments thereof, which is illustrated in the appended drawing(s). It is appreciated that the drawing(s) of the present invention depicts only typical embodiments of the invention and are therefore not to be considered limiting of its scope.

FIG. 1: depicts the NMR spectrum of the four components.

DETAILED DESCRIPTION OF THE INVENTION

Those skilled in the art will be aware that the present disclosure is subject to variations 1H NMR spectrum of IPA based Sanitizer and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

The present disclosure is not to be limited in scope by the specific embodiments described herein, which are intended for the purposes of exemplification only. Functionally equivalent products and methods are clearly within the scope of the disclosure, as described herein.

The present invention provides a method related to the analysis of Hand-rub formulations. In particular, the invention relates to a method based on proton NMR technique i.e., 1H NMR. The invention also relates to the identification and estimation of the components in Hand-rub formulations. The method described in this invention utilizes experimental parameters and derived equations to quantify all four components in just fifteen minutes.

In one embodiment, the present invention provides a method for identifying and quantifying components in a hand-rub formulation, the method comprising:

a) analyzing and characterizing the components by determining position of hydrogen attached to different atoms in each component based on proton NMR technique to obtain chemical shift of hydrogen as ppm peak results, b) quantifying the components using experimental parameters and solving equations with the results obtained in step a) to arrive at the weight % of each component, wherein weight % refers to the percentage by weight of each component in the hand-rub formulation.

In one aspect of the invention, a method of analyzing a sample containing one or more components, which comprises alcohol, peroxide, glycerol, and water, is provided. In one embodiment, the method includes steps of analyzing and characterizing the alcohol, analyzing and characterizing the peroxide, analyzing and characterizing the glycerol, analyzing and characterizing water, and determining the identity and quantity of all the components of the hand-rub formulation i.e., the sample using the results obtained from one or more of the analysis steps. In another embodiment, the equation method comprises generating equations from the results obtained from one or more of the analysis steps and solving them.

In an embodiment, the method is based on proton NMR i.e., 1H NMR. A person skilled in the art will acknowledge that Proton NMR experiment is the most common NMR experiment which involves the study of the hydrogen nucleus when subjected to nuclear magnetic resonance. Being the most sensitive nucleus, proton NMR usually yields sharp signals. At a given radio frequency, each hydrogen atom will need a slightly different magnetic field applied to it to bring it into the resonance condition depending on what exactly it is attached to. Hence, the magnetic field required becomes a very useful guide to the hydrogen atoms environment in the molecule. In an embodiment, the chemical shift of proton NMR spectrum of hand sanitizer used is from 0.0 ppm to 10.0 ppm.

In one embodiment, the method provided includes determining the position of hydrogen attached to the different atoms in all the components. In one aspect of the invention, the position of hydrogen is secondary, if the alcohol in the sample is isopropanol and/or ethanol. In another embodiment, the chemical shift of —OCH— signal of secondary hydrogen of isopropanol at 4.0 ppm is used for quantification of isopropanol. In another aspect of the invention, if the alcohol is methanol, a sharp singlet is observed at 3.3 ppm of —OCH$_3$.

In an embodiment, the appearance of two resolved peaks of glycerol occurs at 3.76 ppm and 3.62-3.50 ppm corresponding to the chemical shift of hydrogen in —OCH— and —OCH$_2$—, respectively. In another embodiment, the chemical shift of —OCH— peak at 3.76 is used for quantification of glycerol content.

In an embodiment, the chemical shift of —OH at 5.5 ppm is used for quantification of hydrogen peroxide. In another embodiment, the chemical shift of —OH at 4.77 ppm is used quantification of water.

In an embodiment, the chemical shifts in the proton NMR at 3.0 ppm to 6.0 ppm corresponding to isopropanol, glycerol, water, and hydrogen peroxide are used for quantification. In another embodiment, the quantitative analysis was carried out using integral intensities obtained under each signal from proton NMR spectrum.

In an embodiment, for hand-rub formulation based on isopropanol, the percentage of each component by weight i.e., weight % has been estimated by following equation:

$$IT=IP+IG+IW+IH$$

where
IT is total integral
IP is Ip×molecular weight of isopropanol,
IG is Ig×molecular weight of glycerol,
IW is Iw×molecular weight of water,
IH si Ih×molecular weight of hydrogen peroxide,
and, Ip, Ig, Iw and Ih are "one proton integral intensity" of iso-propanol, glycerol, water and hydrogen peroxide. "One proton integral intensity" is calculated by corresponding integral intensity of proton NMR spectrum divided by number of protons of the group.
Ip is an integration of 4.0 ppm peak,
Ig is an integration of 3.76 ppm peak,
Iw is an integration of 4.77 ppm peak, divided by two after subtraction of isopropanol and glycerol —OH contributing protons,
Ih is integration of 5.5 ppm peak divided by two
and, weight % of Isopropanol=$(IP/IT) \times 100$, weight % of Glycerol=$(IG/IT) \times 100$, weight % of Water=$(IW/IT) \times 100$, weight % of hydrogen peroxide=$(IH/IT) \times 100$.

In another embodiment, for hand-rub formulation based on ethanol, the percentage of each component by weight i.e., weight % has been estimated by following equation:

$$IT=IE+IG+IW+IH$$

where
IE is Ie×molecular weight of ethanol,
IG is Ig×molecular weight of glycerol,
IW is Iw×molecular weight of water,
IH is Ih×molecular weight of hydrogen peroxide,
and, Ie, Ig, Iw and Ih are "one proton integral intensity" of ethanol, glycerol, water, and hydrogen peroxide. "One proton integral intensity" is calculated by corresponding integral intensity of proton NMR spectrum divided by number of protons of that group.
Ie is an integration of 1.14 ppm peak divided by three,
Ig is an integration of 3.8 to 3.4 ppm peak—Ie×two,
Iw is an integration of 4.7 ppm peak, divided by two after subtraction of ethanol and glycerol —OH contributing protons,
Ih is an integration of 5.4 ppm peak divided by two,
And, weight % of Ethanol=$(IE/IT) \times 100$, weight % of Glycerol=$(IG/IT) \times 100$, weight % of Water=$(IW/IT) \times 100$, weight % of hydrogen peroxide=$(IH/IT) \times 100$.

In an embodiment, the method based on proton NMR provides identification and estimation of all components in hand sanitizer formulations. In another embodiment, the method provides equations for estimation of components in hand sanitizer.

EXAMPLE

Example 1

WHO recommended Hand-rub Formulation with Formulation II having final composition (v/v) of 75% of Iso-propanol, 0.125% of Hydrogen peroxide, 1.45% of Glycerol and Sterile distilled or boiled cold water was prepared and analyzed by proton NMR method to identify all components present in the formulation by following characteristic peaks. Iso-propanol was identified by the chemical shift of —OCH— signal of secondary hydrogen at 4.0 ppm, the appearance of two resolved peaks of glycerol were observed at 3.76 ppm and 3.62 to 3.50 ppm corresponding to the chemical shift of hydrogen in —OCH— and —OCH$_2$— respectively, the chemical shift of —OH was visible at 5.5 ppm of hydrogen peroxide, and the chemical shift of —OH at 4.77 ppm indicated the presence of water.

Example 2

Iso-propanol, glycerol, hydrogen peroxide, and water in a formulation prepared by other group (Fuel department) were quantified by derived equations using integration of their characteristics signals and it was found that 71.3%, 2.3%, 0.18%, 26.2% of Iso-propanol, Hydrogen peroxide, Glycerol, and water respectively was present against actual concentration values of 73.3%, 2.3%, 0.19% and 24.81% of Iso-propanol, Hydrogen peroxide, Glycerol, and water respectively given by the Automotive department formulator.

Example 3

Iso-propanol, glycerol, hydrogen peroxide, and water in a laboratory prepared blend 1 which was prepared by other group was quantified and concentration of Iso-propanol, Hydrogen peroxide, Glycerol, and water was found as 51.2%, 9.2%, 0.2%, 39.4% respectively against actual concentration values of 53.1%, 8.5%, 0.14% and 38.26% of Iso-propanol, Hydrogen peroxide, Glycerol, and water respectively given by formulator.

Concentration of Iso-propanol, glycerol, and water found in blend 2 was 61.2%, 6.2% and 32.6% against actual concentrations of 63.9%, 5.9% and 29.94% respectively in blend 2. Estimation of hydrogen peroxide ($H_2O_2$) was not possible in blend 2 due to high concentration of $H_2O_2$. At this concentration, the hydrogen peroxide and water peaks coalesce to form a single peak that is broadened. This phenomenon is attributed to the exchange of protons between water and hydrogen peroxide. As the concentration of hydrogen peroxide increases, the rate of proton exchange between water and hydrogen peroxide becomes significant, and as a result, a single broadened peak is observed.

Example 4

WHO recommended Hand-rub Formulation with Formulation I having final composition (wt/wt %) of 76.5% of ethanol, 0.20% of Hydrogen peroxide, 2.5% of Glycerol, and 20.8 of Sterile distilled or boiled cold water was prepared and concentration of Ethanol, Hydrogen peroxide, Glycerol, and water estimated by NMR method of the present invention was 75.4%, 0.18%, 2.4% and 23.02% respectively.

Example 5

A commercial hand sanitizer was analyzed and iso-propanol, glycerol and water were found at concentrations of 45.2%, 1.10%, and 52.0% respectively, while 1.7% of methanol which is a toxic chemical was observed. Five more commercial samples were analyzed by this method and the iso-propanol concentration was found to be below WHO recommended concentration for COVID-19 hand sanitizers.

TECHNICAL ADVANTAGES OF THE INVENTION

1. Designed experiments and solvent system for separating all four components.
2. No organic solvent or standard used in this method.
3. Quick and less time taking (one sample in just fifteen minutes).
4. Derived the equations for quantification.
5. Able to identify the presence of non-recommended/additional components.

The invention claimed is:
1. A method comprising:
providing a hand-rub formulation comprising an alcohol, a peroxide, glycerol, and water, wherein the alcohol is ethanol or isopropanol, and wherein the peroxide is hydrogen peroxide;
measuring a chemical shift by determining a position of hydrogen attached to different atoms in the alcohol, the peroxide, the glycerol, and the water using a proton NMR spectrum;
using the chemical shift of —OCH— signal of a secondary hydrogen at 4.0 ppm for quantification of alcohol, the chemical shift of —OCH— peak at 3.76 ppm for quantification of glycerol, the chemical shift of —OH at 5.5 ppm for quantification of hydrogen peroxide, and the chemical shift of —OH at 4.77 ppm for quantification of water;
calculating a weight % of the alcohol, the peroxide, the glycerol, and the water based on the alcohol by an equation IT=IP+IG+IW+IH, and wherein
IT is a total integral,
IP is Ip×molecular weight of the alcohol,
IG is Ig×molecular weight of the glycerol,
IW is Iw×molecular weight of the water,
IH is Ih×molecular weight of the peroxide,
wherein Ip, Ig, Iw and Ih are "one proton integral intensity" of the alcohol, the glycerol, the water, and the peroxide and is calculated by corresponding integral intensity of the proton NMR spectrum divided by number of protons of the group, thereby quantifying at once the alcohol, the peroxide, the glycerol, and the water in the hand-rub formulation;
wherein the method is carried out in absence of an organic solvent or a standard, and, wherein the method further identifies presence of non-recommended components present in the hand-rub formulation, thereby differentiating a genuine and a spurious hand-rub formulations.

2. The method as claimed in claim 1, further comprising quantifying, weight % of the isopropanol, the hydrogen peroxide, the glycerol, and the water in the hand-rub formulation based on isopropanol by an equation IT=IP+IG+IW+IH, and wherein
IT is a total integral,
IP is Ip×molecular weight of the isopropanol,
IG is Ig×molecular weight of the glycerol,
IW is Iw×molecular weight of the water,
IH is Ih×molecular weight of the hydrogen peroxide,
wherein Ip, Ig, Iw and Ih are "one proton integral intensity" of the isopropanol, the glycerol, the water, and the hydrogen peroxide and is calculated by corresponding integral intensity of a proton NMR spectrum divided by number of protons of the group.

3. The method as claimed in claim 2, wherein
Ip is an integration of 4.0 ppm peak,
Ig is an integration of 3.76 ppm peak,
Iw is an integration of 4.77 ppm peak divided by two after subtraction of isopropanol and glycerol —OH contributing protons,
Ih is an integration of 5.5 ppm peak divided by two.

4. The method as claimed in claim 2, wherein, weight % of isopropanol=($IP/IT$)×100, weight % of glycerol=($IG/IT$)×100, weight % of water=($IW/IT$)×100, weight % of hydrogen peroxide=($IH/IT$)×100.

5. The method as claimed in claim 1, further comprising quantifying, weight % of the ethanol, the hydrogen peroxide, the glycerol, and the water in the hand-rub formulation based on the ethanol by an equation IT=IE+IG+IW+IH, and wherein IE is Ie×molecular weight of ethanol,
IG is Ig×molecular weight of glycerol,
IW is Iw×molecular weight of water,
IH is Ih×molecular weight of hydrogen peroxide,
wherein Ie, Ig, Iw and Ih are "one proton integral intensity" of the ethanol, the glycerol, the water, and the hydrogen peroxide and is calculated by corresponding integral intensity of a proton NMR spectrum divided by number of protons of that group.

6. The method as claimed in claim 5, wherein
Ie is an integration of 1.14 ppm peak divided by three,
Ig is an integration of 3.8 to 3.4 ppm peak—Ie×two,
Iw is an integration of 4.7 ppm peak divided by two after subtraction of ethanol and glycerol —OH contributing protons,
Ih is an integration of 5.4 ppm peak divided by two.

7. The method as claimed in claim 5, wherein weight % of ethanol=$(IE/IT) \times 100$, weight % of glycerol=$(IG/IT) \times 100$, weight % of water=$(IW/IT) \times 100$, weight % of hydrogen peroxide=$(IH/IT) \times 100$.

8. The method as claimed in claim 1, wherein the chemical shift of the proton NMR spectrum of the hand-rub formulation used is in a range of 0.0 ppm to 10.0 ppm.

9. The method as claimed in claim 1, wherein the method further comprises identifying methanol in the hand-rub formulation.

10. The method as claimed in claim 9, wherein a sharp singlet is observed at 3.3 ppm of —$OCH_3$ for the methanol.

* * * * *